(12) United States Patent
Sugiyama et al.

(10) Patent No.: US 7,107,849 B2
(45) Date of Patent: Sep. 19, 2006

(54) VIBRATION SOURCE PROBE SYSTEM

(75) Inventors: Takeshi Sugiyama, Aichi (JP); Noboru Kawaguchi, Aichi (JP); Masanao Ohwaki, Tokyo (JP); Takefumi Zaima, Tokyo (JP); Yasuhiro Yamashita, Nagano (JP)

(73) Assignee: Chubu Electric Power Co., Ltd., Aichi (JP)

( * ) Notice: Subject to any disclaimer, the term of this patent is extended or adjusted under 35 U.S.C. 154(b) by 0 days.

(21) Appl. No.: 10/459,592

(22) Filed: Jun. 12, 2003

(65) Prior Publication Data

US 2004/0035209 A1 Feb. 26, 2004

(30) Foreign Application Priority Data

Aug. 22, 2002 (JP) ............................. 2002-242220

(51) Int. Cl.
*G01H 1/00* (2006.01)

(52) U.S. Cl. .......................................... 73/592; 73/587
(58) Field of Classification Search .................. 73/587, 73/594, 592, 40.5 A, 577, 579, 583; 367/127, 367/129, 906
See application file for complete search history.

(56) References Cited

U.S. PATENT DOCUMENTS

| | | | | |
|---|---|---|---|---|
| 3,838,593 A | * | 10/1974 | Thompson | 73/40.5 A |
| 3,875,381 A | * | 4/1975 | Wingfield et al. | 73/587 |
| 4,033,179 A | * | 7/1977 | Romrell | 73/594 |
| 4,459,851 A | * | 7/1984 | Crostack | 73/587 |
| 4,481,818 A | * | 11/1984 | Hellqvist | 73/587 |
| 4,592,034 A | * | 5/1986 | Sachse et al. | 73/587 |
| 4,819,753 A | * | 4/1989 | Higo et al. | 73/587 |
| 4,885,725 A | * | 12/1989 | McCarthy et al. | 367/127 |
| 5,270,950 A | * | 12/1993 | Cowley et al. | 73/587 |
| 5,293,555 A | * | 3/1994 | Anthony | 73/587 |
| 5,754,497 A | * | 5/1998 | Tapia-Egoavil | 73/587 |
| 5,781,505 A | * | 7/1998 | Rowland | 367/127 |
| 5,979,239 A | * | 11/1999 | Youngquist et al. | 73/592 |
| 6,065,342 A | * | 5/2000 | Kerr et al. | 73/587 |
| 6,240,051 B1 | * | 5/2001 | Bunks | 367/127 |
| 6,550,332 B1 | * | 4/2003 | Lee | 73/589 |

FOREIGN PATENT DOCUMENTS

DE 3116586 A1 * 3/1984

* cited by examiner

*Primary Examiner*—Hezron Williams
*Assistant Examiner*—Nashmiya Fayyaz
(74) *Attorney, Agent, or Firm*—Takeuchi & Kubotera, LLP (57) ABSTRACT

A vibration source probe system for detecting the surface waves of vibration coming over the ground or the floor of a building and specifying and displaying a vibration source at a factory or on a road.

The position of a vibration source is estimated from a phase difference or arrival time difference between vibrations of surface waves detected by the vibration sensors which are separated from each other by a predetermined distance, an image near the estimated position of the vibration source is picked up by a camera, and the estimated position of the vibration source is displayed on the image displayed on the display screen of a personal computer.

10 Claims, 7 Drawing Sheets

VIBRATION SOURCE PROBE SYSTEM

BACKGROUND OF THE INVENTION

1. Field of the Invention

The present invention relates to a vibration source probe system for specifying and displaying the source of a vibration which is generated on a road or at a factory.

2. Description of the Prior Art

Low-frequency vibrations are generated from machine tools and the like installed at a factory together with noises. These vibrations are perceived as vibrations from the ground or the floor of a building. On a road or in a house near an intersection where there is heavy traffic, vibrations coming from the above road together with noises generated by the passage of trucks cause a problem.

In general, as the source of a vibration is identical to the source of a noise in most cases, the method of estimating the source of a vibration by sampling a noise from the above machine tool or truck to specify the source of the noise is effective. However, when many machine tools are installed near walls and surrounded by partitions or when there is a wall or building between a place where the source of a vibration passes, such as an intersection and a place where a vibration is perceived, a noise is reflected by the above reflector complicatedly, thereby making it difficult to specify the source of the noise itself. Since a sound generated together with a vibration when a truck or the like runs over a depression or manhole in a road has a very low frequency, it is difficult to locate the source of the sound.

Meanwhile, there is known a method of specifying a seismic center as means of specifying the source of a vibration. This method is to calculate the distances between a plurality of measurement points and the seismic center from a difference (initial fine movement time) between the arrival times of the P wave (vertical wave) and S wave (horizontal wave) of seismic waves measured by a seismograph at the plurality of measurement points so as to obtain the seismic center from the above calculated distances from the measurement points. It is possible to obtain the coordinates of the seismic center if there are at least three measurement points.

However, a vibration from a vibration source at the factory or on the road, such as the above machine tool or truck is generally a continuous vibration (surface wave) which is different from the P wave or S wave corresponding to the main vibration of the seismic waves. In addition, the vibration to be detected is mixed with vibrations from a plurality of vibration sources, thereby making it impossible to specify the starting point of the vibration from a specific vibration source. Therefore, even if the above method of obtaining the seismic center is directly employed, it is difficult to specify the above vibration source.

SUMMARY OF THE INVENTION

It is an object of the present invention which has been made in view of the problems of the prior art to provide a vibration source probe system which can specify and display the source of a vibration at a factory or on a road by detecting the surface wave of the vibration coming from the ground or the floor of a building.

According to a first aspect of the present invention, there is provided a vibration source probe system which comprises vibration detection means having at least three vibration sensors arranged on the same plane, and vibration source estimation means for estimating the source of a vibration from phase differences or arrival time differences among vibrations of surface waves (to be accurate, the time-series waveforms of vibration accelerations) detected by the vibration sensors to specify the source of the above vibration.

When at least three vibration sensors are arranged on the same plane, it is a matter of course to exclude a case where a plurality of vibration sensors are placed at the same location and a case where all the vibration sensors are arranged on one straight line.

According to a second aspect of the present invention, there is provided a vibration source probe system wherein a pair of vibration sensors which are separate from each other by a predetermined distance are arranged on two straight lines crossing each other at a right angle, for example, a pair of vibration sensors are placed at $X1=(L_1/2,0)$ and $X2=(-L_1/2,0)$ on the X axis and another pair of vibration sensors are arranged at $Y1=(0,L_2/2)$ and $Y2=(0, -L_2/2)$ on the Y axis, to obtain arrival time differences between vibrations detected by the above pairs of vibration sensors in order to estimate the source of a vibration from the above arrival time differences.

According to a third aspect of the present invention, there is provided a vibration source probe system wherein the vibration detection means detects the above vibration at predetermined time intervals to estimate the movement of the source of the vibration.

According to a fourth aspect of the present invention, there is provided a vibration source probe system which comprises means of measuring the absolute position on the ground of the above vibration detection means. The absolute position on the ground of the source of the vibration is computed from the position of the above measured vibration detection means.

According to a fifth aspect of the present invention, there is provided a vibration source probe system wherein the above vibration detection means is moved to a plurality of points to detect a vibration at a plurality of positions, thereby making it possible to improve the measurement accuracy of the position of the source of the vibration.

According to a sixth aspect of the present invention, there is provided a vibration source probe system wherein the above vibration detection means is made rotatable so as to detect a vibration at a plurality of angles by turning the vibration detection means, thereby improving the measurement accuracy of the position of the source of the vibration.

According to a seventh aspect of the present invention, there is provided a vibration source probe system which comprises image pick-up means for picking up an image near the above estimated source of a vibration and display means for displaying the position of the above estimated source of the vibration on the above picked up image. Thereby, the position of the vibration source can be clearly recognized.

According to an eighth aspect of the present invention, there is provided a vibration source probe system wherein either one or both of a time change in the level and the frequency spectrum of vibration detected by the vibration sensors is displayed on the display means.

According to a ninth aspect of the present invention, there is provided a vibration source probe system wherein the color of a symbol indicating the position of a vibration source displayed on the display means is changed by the level or frequency of vibration detected by the above vibration sensors. Thereby, even when there are a plurality of vibration sources, not only the positions of the vibration sources but also the levels and frequency characteristics of vibrations can be displayed, thereby making it possible to judge the characteristics of the vibration sources visually. According to a tenth aspect of the present invention, there is provided a vibration source probe system wherein the movement of the above estimated vibration source is displayed on the above display means.

The above and other objects, advantages and features of the invention will become apparent from the following description when taken in conjunction with the accompanying drawings.

DETAILED DESCRIPTION OF THE PREFERRED EMBODIMENTS

Preferred embodiments of the present invention will be described hereinbelow with reference to the accompanying drawings.

Figure 1:
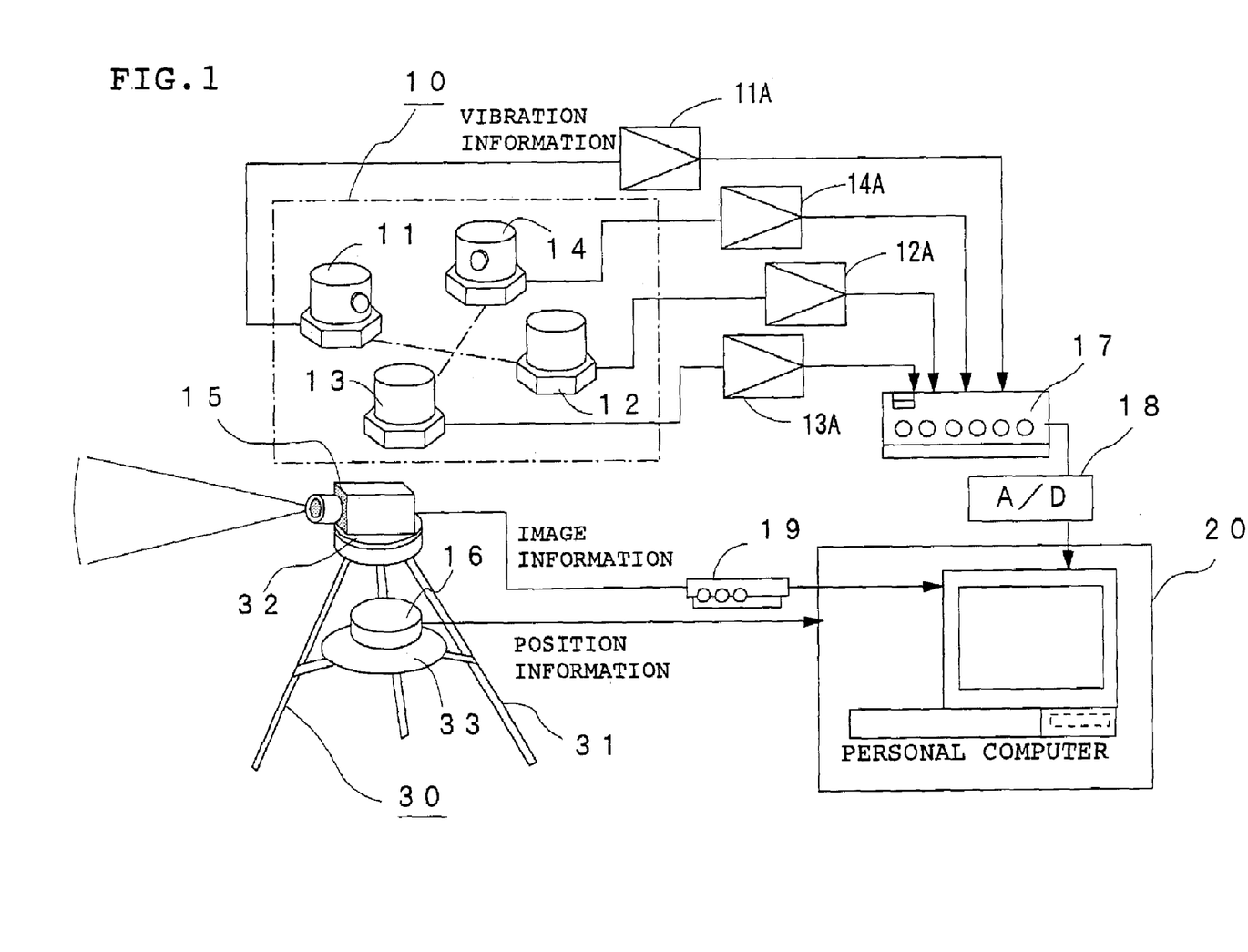
FIG. 1 is diagram showing the constitution of a vibration source probe system according to an embodiment of the present invention.

FIG. 1 is a diagram showing the constitution of a vibration source probe system according to an embodiment of the present invention. Reference numeral 10 denotes vibration detection means consisting of vibration sensors 11 to 14 such as vibration pick-ups or acceleration sensors arranged on the same plane, 11A to 14A amplifiers for amplifying the time-series waveforms of vibration accelerations detected by the above vibration sensors 11 to 14 (to be referred to as "output signals" hereinafter), 15 a CCD camera for picking up an image near the position of a vibration source (to be referred to as "camera" hereinafter), 16 GPS for specifying the ground position of the above vibration detection means 10, 17 a low-pass filter, 18 an A/D converter for converting the above output signal (analog signal) which has been screened by the low-pass filter 17 into a digital signal, and 19 a video input/output unit for converting the image signal (analog signal) of the above camera 15 into a digital signal.

Denoted by 20 is a personal computer as computing and display means for estimating the position of the vibration source and displaying it, 30 a camera base consisting of a support member 31 composed of a tripod and a rotary frame 32 mounted on top of the support member 31. The camera 15 is mounted on the above rotary frame 32 of the camera base 30. GPS 16 is mounted on a mounting plate 33 installed below the rotary frame 32 of the above camera base 30.

Figure 2A:
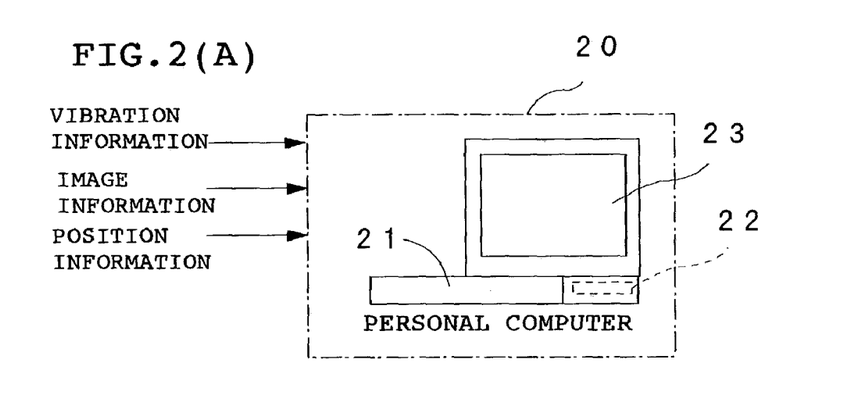
FIG. 2 is a functional block diagram of the storing and computing unit of a personal computer according to the embodiment of the present invention.
Figure 2B:
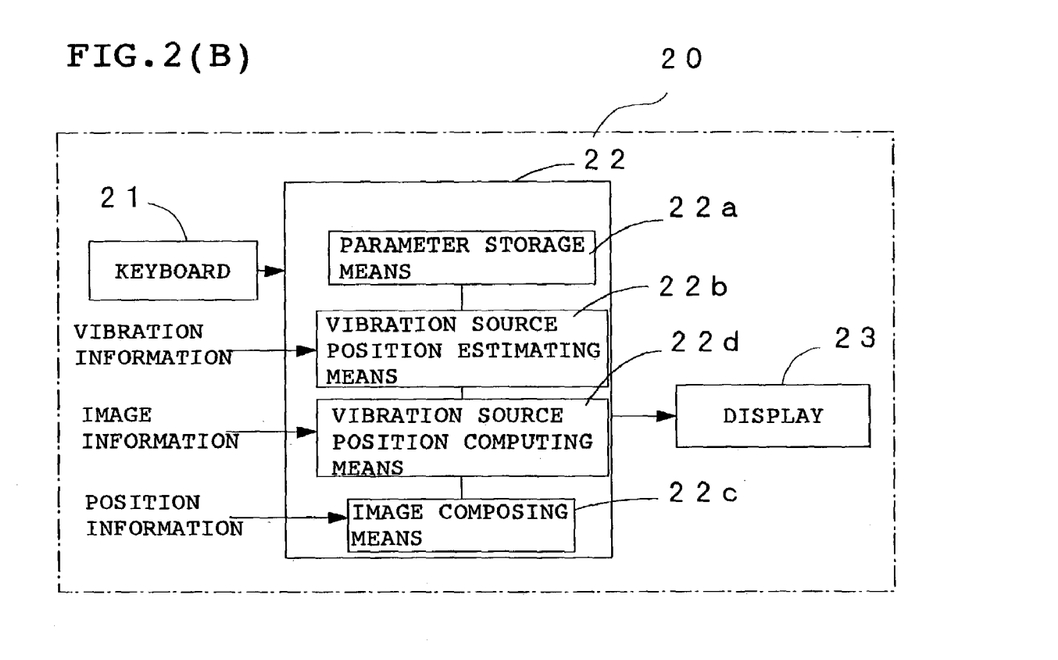

As shown in FIG. 2(A) and FIG. 2(B), the above personal computer 20 comprises a keyboard 21 as input means of inputting measurement conditions such as measurement parameters, display 23 as display means, and storing and computing unit 22 which includes parameter storage means 22a for storing the above measurement parameters, vibration source position estimating means 22b for estimating the position of a vibration source from the output signals of the vibration sensors 11 to 14 which have been converted from analog to digital, image composing means 22c for creating an image by adding an image of the estimated position of the vibration source to an image from the above camera 15 and sending it to the display 23 as display means, and vibration source position computing means 22d for computing the absolute position on the ground of the vibration source based on a signal from the above GPS 16 and the estimated position of the vibration source, estimates the position of the vibration source from vibration information detected by the vibration detection means 10 and displays the estimated position of the vibration source on the image near the vibration source picked up by the above camera 15 and displayed on the display 23.

Figure 3:
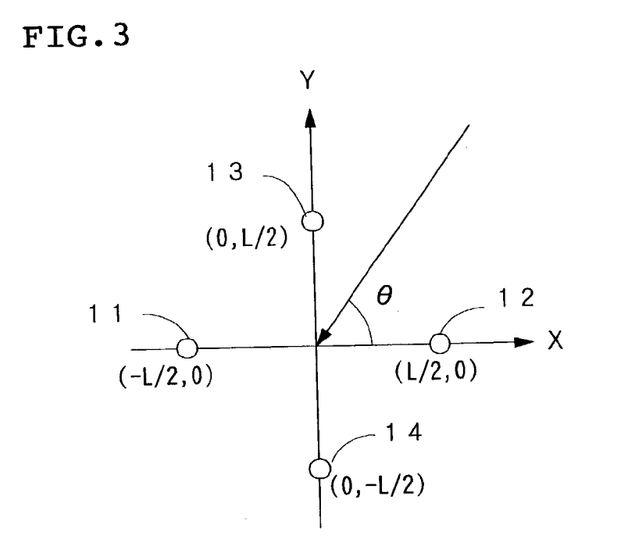
FIG. 3 is a diagram showing the arrangement of vibration sensors.

Since the vibration source probe system according to the present invention estimates the position of a vibration source by detecting a vibration (surface wave) coming over the ground or the floor of a building from a vibration source, at least three vibration sensors are arranged on the same plane and the vibration source is estimated from phase differences or arrival time differences among vibrations of surface waves detected by the above vibration sensors. In this example, the vibration sensors 11 to 14 constituting the vibration detection means 10 are placed at points (L/2,0) and (−L/2,0) on the X axis and at points (0, L/2) and (0, −L/2) on the Y axis intersecting the X axis at a right angle as shown in FIG. 3, thereby forming a pair of vibration sensors (11, 12) and a pair of vibration sensors (13, 14) which are separated from each other by a distance L. Output signals from the pair of vibration sensors (11, 12) and the pair of vibration sensors (13, 14) are frequency analyzed to obtain arrival time differences Dx and Dy at a predetermined frequency "f" from the cross spectrum Pij(f) of a signal applied to the vibration sensors 11 to 14 and further compute the phase angle information Ψ(rad) of the above frequency as a vibration source direction θ shown in the figure from the following equation (1).

$$\theta = \tan^{-1}\left(\frac{Dy}{Dx}\right) \quad (1)$$

More specifically, the above time delay Dij is computed by obtaining the cross spectrum Pij (f) of the signal applied to a pair of vibration sensors (i, j) (a pair of vibration sensors (11, 12) or a pair of vibration sensors (13, 14)) and using the phase angle information Ψ(rad) of the above frequency "f" from the following equation (2).

$$D_{ij} = \frac{1}{2\pi f}\Psi[P_{ij}(f)] \text{ (sec)} \quad (2)$$

The above vibration source direction θ can be computed every frequency "f".

The interval L between the pair of vibration sensors (11, 12) and the pair of vibration sensors (13, 14) is determined according to the main frequency range of a vibration to be measured. In this embodiment, a vibration having a peak at 3 Hz to 20 Hz which is perceived uncomfortable by people is analyzed, and the above interval L is set to 0.6 m in consideration of the vibration propagation speed over the ground so that the above vibration can be measured at a high sensitivity.

Figure 4:
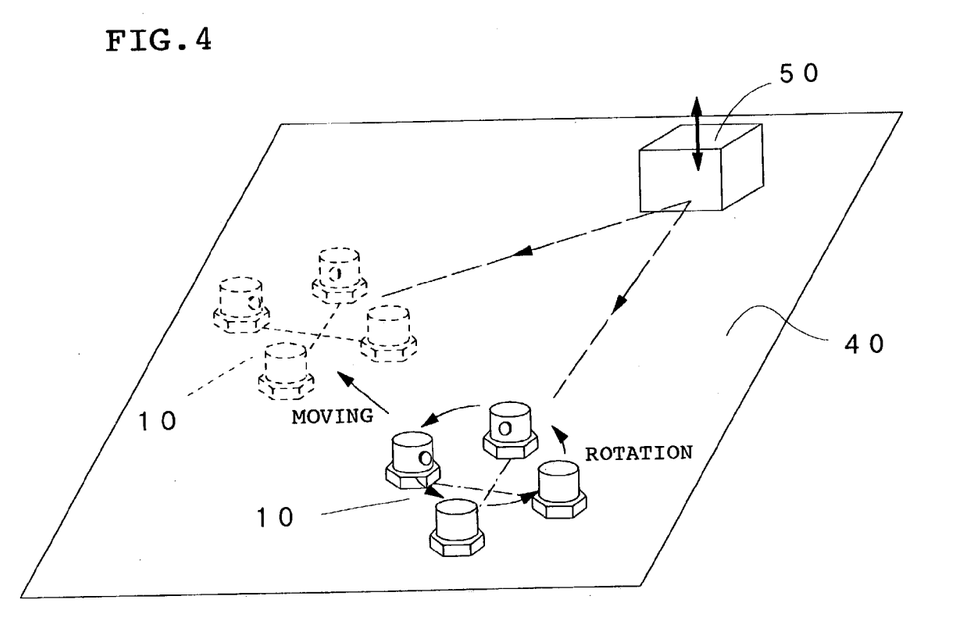
FIG. 4 is a diagram for explaining the movement of vibration detection means.

Although the above vibration source direction θ can be obtained from one time of measurement, in this embodiment, it is measured at a plurality of positions by moving the vibration detection means 10 and the camera base 30 to a plurality of points on the surface of the ground 40 or at a plurality of angles by turning the vibration detection means 10 and the camera base 30 as shown in FIG. 4 in order to improve the measurement accuracy of the direction θ of the vibration source 50.

Since the vibration source can be predicted, if the direction θ of the vibration source 50 is known, the vibration source can be specified from the above θ with reference to a map of a location near the measurement point and an image picked up by the above camera 15 without obtaining the coordinates of the position of the vibration source 50. Particularly when the vibration source 50 is assumed to be a mobile body, it is effective in specifying the vibration source 50 to obtain time changes in the above vibration source direction θ rather than the coordinates of the position of the vibration source 50 by omitting the above measurement at the plurality of angles.

To obtain the coordinates of the position of the vibration source 50, the above direction θ of the vibration source must be measured at a plurality of positions. Stated more specifically, the vibration detection means 10 is turned at the same measurement point to measure the direction $\theta_1$ of the vibration source at a plurality of angles to specify it and then the vibration detection means 10 is moved to a plurality of positions to measure the direction $\theta_1$ of the vibration source at a plurality of angles by turning the vibration detection means 10 as described above to specify the vibration source directions $\theta_2, \theta_3, \ldots, \theta_k$ ($k \geq 2$), thus obtaining the coordinates of the position of the vibration source from the positions of the measurement points and the above $\theta_1$ to $\theta_k$. In this embodiment, the absolute position on the ground of each measurement point detected by the GPS 16 and computed by the vibration source position computing means 22d is the position of each measurement point. The position of each measurement point may be a relative position from a reference point provided separately or the first measurement point as a reference point.

Figure 5:
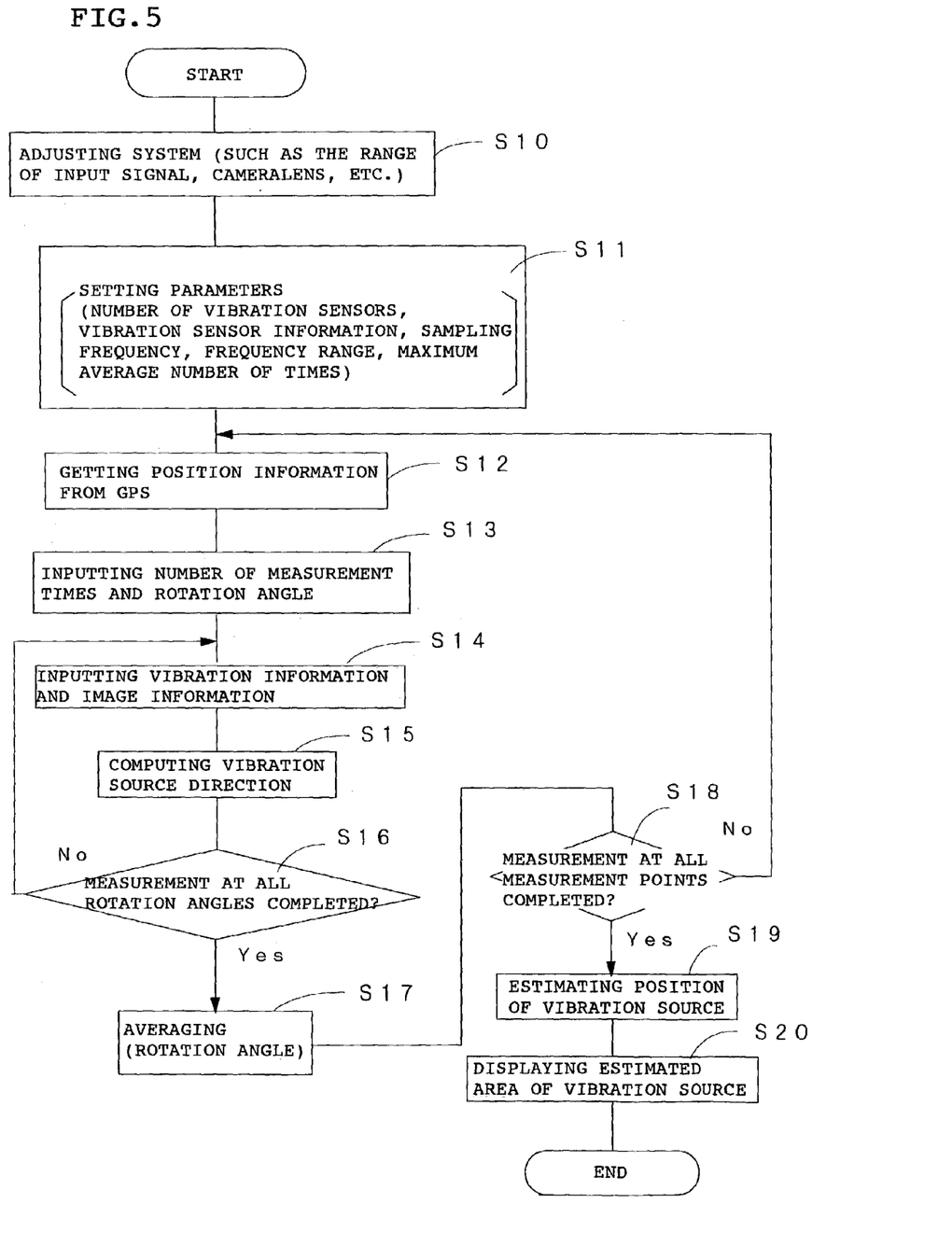
FIG. 5 is a flow chart of a vibration source probe method according to an embodiment of the present invention.

A description is subsequently given of the method of investigating a vibration source using the above vibration source probe system with reference to a flow chart of FIG. 5.

First, the vibration sensors 11 to 14 of the vibration detection means 10 are placed at positions where they can detect a vibration from a vibration source, the camera base 30 mounting the camera 15 and GPS 16 is installed near the vibration detection means 10, and then the ranges of the input signals and the lenses of the camera are adjusted (step S10). Thereafter, parameters such as the number of vibration sensors and the sampling frequency are input into the parameter storage means 22a of the storing and computing unit 22 of the personal computer 20 (step S11). The above parameters include not only the number of measurement points, the number of vibration sensors and the sampling frequency but also information on the arrangement of the vibration sensors, the pass frequency range of an unshown filter and the maximum average number of times. Initial values of these parameters are preset in the parameter storage means 22a. In general, only changed parameters are input.

Subsequently, the positions of the vibration sensors 11 to 14, that is, the absolute positions on the ground of the vibration detection means 10 are measured by GPS 16 mounted on the camera base 30 installed near the vibration detection means 10 and input into the personal computer 20 (step S12), and then the number of measurement times at the above measurement point and the rotation angles of the vibration sensors 11 to 14 and the camera base 30 are input into the personal computer 20 by the keyboard 21 (step S13). The vibration level (vibration information) and image information may be detected by turning the vibration sensors 11 to 14 and the camera base 30 each time measurement is made or by turning the vibration sensors 11 to 14 and the camera base 30 after measurement is made a plurality of times at the same angle.

In this embodiment, the vibration sensors 11 to 14 and the camera 15 are turned at angles of 0° (initial position), 90°, 180° and 270° to detect and sample vibration information and image information one time at each position, and the above detected and sampled vibration information and image information are input into the personal computer 20 (step S14). That is, in this embodiment, the measurement conditions are set to carry out measurement four times at that measurement point. Vibration waveform signals which are output signals from the vibration sensors 11 to 14 are amplified by the amplifiers 11A to 14A, screened by the low-pass filter 17 and converted into digital signals by the A/D converter 18. An image signal from the camera 15 is converted into a digital signal by the video input/output unit 19 and applied to the personal computer 20.

The personal computer 20 carries out computation to estimate the position of the vibration source using vibration information from the above vibration sensors 11 to 14 and the expression of the vibration source direction θ, $\theta = \tan^{-1}(D_y/D_x)$ (step S15).

It is then judged whether measurement at all the frame rotation angles is completed (step S16). When it is not completed, the vibration sensors 11 to 14 and the camera 15 are turned at 90° and the routine returns to step S14 to detect and sample vibration information and image information at the next rotation angle. When measurement at all the frame rotation angles is completed, the rotary frame 32 is returned to the initial position, and all the values of the vibration source direction θ obtained at that measurement point are averaged (step S17).

Figure 6:
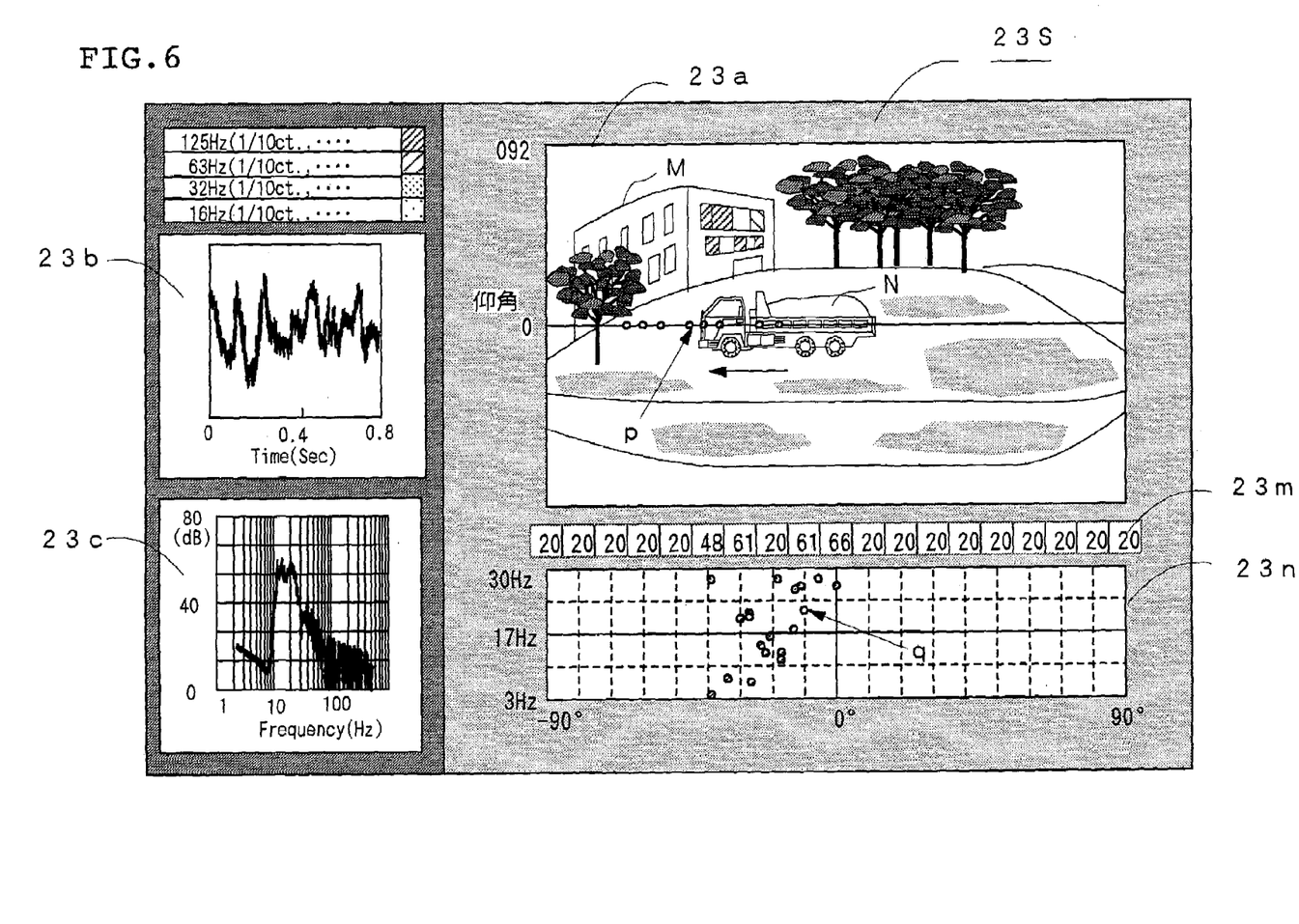
FIG. 6 is a diagram showing an example of a display screen according to the present invention.

Thereafter, it is judged whether measurement at all the measurement points is completed or not (step S18). When it is not, the vibration detection means 10 is moved to the next measurement point $P_i$ to carry out the operations of the steps S12 to S17 in order to specify the vibration source direction $\theta_i$ at that position. When measurement at all the measurement points ($P_1$ to $P_k$) is completed, the position of the vibration source is estimated from data on the vibration source directions $\theta_1$ to $\theta_k$ at the above measurement points (step S19), and the best image of the estimated position of the vibration source is selected, displayed in a vibration source display section 23a formed on the display screen 23S of the display 23 and indicated by a symbol p such as a circle as shown in FIG. 6 (step S20).

When a vibration waveform display section 23b and a frequency characteristic display section 23c are created in the above display screen 23S to display time changes in the level and the frequency spectrum of the detected vibration together with the above image, it is possible to provide clear information on the vibration characteristics of the vibration source.

Further, when the color of the circle (symbol) "p" indicating the position of the vibration source displayed on the image of the above vibration source display section 23a is changed by the level or frequency of the detected vibration, a level direction estimation section 23m indicating the level of vibration with respect to horizontal angle (vibration source direction θ) or the level of vibration acceleration is created in the above display screen 23S, a vibration frequency direction estimation section 23n showing horizontal angle on the horizontal axis and frequency on the vertical axis is created to display a circle (symbol) "q" colored according to the level of vibration, even if there are a plurality of vibration sources, not only the positions of the vibration sources but also the levels and frequency characteristics of vibrations in each direction can be acquired, thereby making it possible to judge the characteristics of the vibration sources visually.

When the color of the symbol "p" indicative of the position of the vibration source displayed on the image in the above vibration source display section 23a is changed by the level or frequency of the detected vibration, if there are a plurality of vibration sources, not only the position of each vibration source but also the levels and frequency characteristics of vibrations can be displayed, thereby making it possible to judge the characteristics of the vibration sources visually.

The coordinates of the estimated position of the vibration source may be displayed on the above display screen 23S at the same time. The above coordinates may be values from the preset origin (0,0) or the coordinates of the absolute position on the ground of the above estimated position of the vibration source calculated based on the position of the vibration detection means 10 measured by the above GPS 16.

When the estimated vibration source is moving, as shown in FIG. 6, the movement of the estimated vibration source may be displayed on the image of the above vibration source display section 23a. For example, the position of the symbol "p" indicating the position of the vibration source displayed on the image of the above vibration source display section 23a is moved, or an image of the moving symbol "p" is displayed as a dynamic image. Thereby, when there is a building M where a large-sized machine tool is installed as a vibration source near an intersection, it can be presumed with certainty whether the cause of vibration perceived on the road or in house near the intersection is the above building M or not. That is, when it is judged that all the vibration sources having a predetermined level or more are moving out of the estimated vibration sources, it can be presumed that the cause of vibration is a truck N passing through the intersection and not the above building M. When there is a fixed vibration source having a predetermined level or more near the above building M, it is presumed that the above building M is one of the vibration sources.

Thus, according to this embodiment, the direction θ of the vibration source is estimated from an arrival time difference between output signals from the pair of vibration sensors (11, 12) separated from each other by a distance L and an arrival time difference between output signals from the pair of vibration sensors (13, 14) separated from each other by the distance L, an image near the estimated position of the vibration source is picked up by the camera 15, and the estimated position of the vibration source is displayed on the above image displayed on the display screen 23S of the display 23 of the personal computer 20. Therefore, the position of the vibration source can be specified and displayed accurately.

Measurement is carried out by moving the above sensors 11 to 14 and the camera 15 to a plurality of positions and turning the vibration sensors 11 to 14 and the camera 15 at a plurality of angles at the same measurement point, whereby the measurement accuracy of the vibration source direction θ can be improved and the position of the vibration source 50 can be specified through measurement at a plurality of positions.

Figure 7:
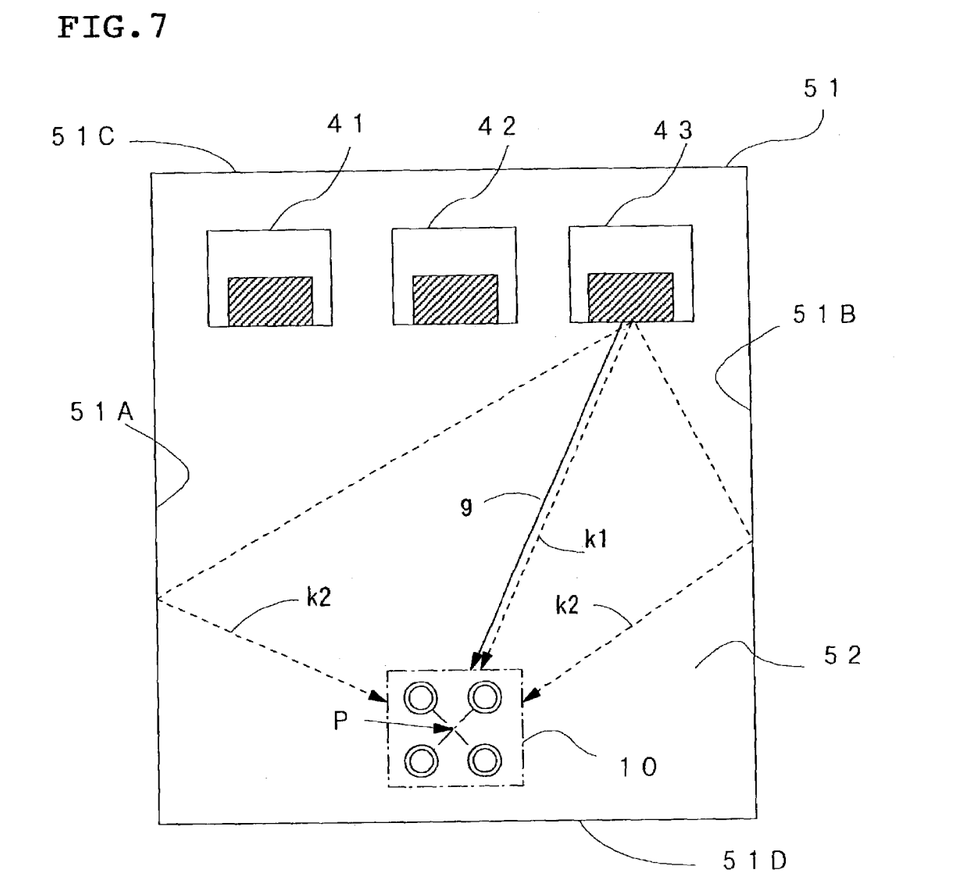
FIG. 7 is a diagram showing an application example of the present invention.

Since the vibration source is estimated from the vibrations of surface waves detected by the vibration sensors 11 to 14 in this embodiment, it can be estimated more accurately than when the vibration source is estimated by the measurement of noise. For example, when there are a plurality of outside units 41 to 43 of an air conditioner in a room 51 surrounded by walls 51A to 51D and one of them generates big noise and vibration as shown in FIG. 7, not only a noise $k_1$ directly coming from the outside unit 43 in concern but also noises $k_2$ reflected by the walls 51A and 51B on both sides reach a measurement point P, thereby making it difficult to specify the outside unit 43.

In contrast to this, as reflected vibration is not so large as reflected noise in the case of vibration from the outside unit 43, vibration "g" over the floor 52 becomes dominant, whereby the outside unit 43 can be easily specified by installing the above vibration detection means 10 at the above measurement point P to estimate the direction of the vibration source.

Even when a truck or the like runs over a depression or manhole on the road, the depression or manhole on the road which causes a vibration can be specified by detecting the vibration.

Further, since the frequency band of the vibration of surface waves detected by the vibration sensors 11 to 14 is narrower than the frequency band of noise, a signal processing circuit and a memory circuit can be reduced in size, thereby making it possible to increase the signal processing speed and downsize the apparatus.

Figure 8A:
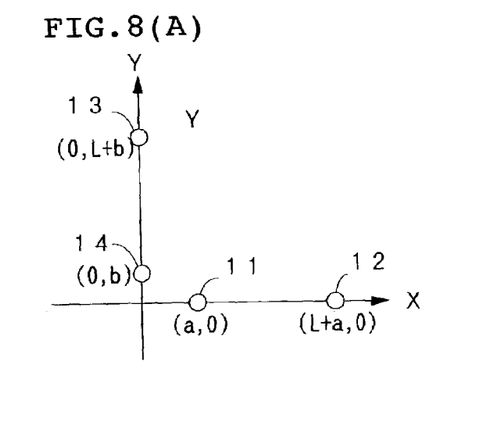
FIG. 8 is a diagram showing another example of the arrangement of vibration sensors according to the present invention.
Figure 8B:
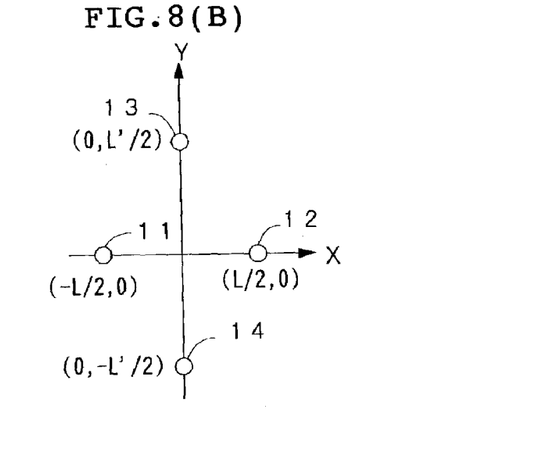

In the above embodiment, four vibration sensors are arranged symmetrical about the X axis and the Y axis. When, the four sensors cannot be arranged symmetrical as described above according to the situation of a site, as shown in FIG. 8(A), the pair of vibration sensors (11, 12) and the pair of vibration sensors (13, 14) may be moved on the X axis and the Y axis, respectively. Also, as shown in FIG. 8(B), the distance between the vibration sensors 11 and 12 and the distance between the vibration sensors 13 and 14 may be made different from each other. The angle between the pair of vibration sensors (11, 12) and the angle between the pair of vibration sensors (13, 14) do not need to be always 90° but preferably 90° because when it is not 90°, the conversion of coordinates must be carried out to obtain the direction θ of the vibration source.

The number of vibration sensors is not limited to 4. The number of pairs of vibration sensors separate from each other by a predetermined distance for obtaining a phase difference or arrival time difference between vibrations of surface waves is at least two and these pairs of vibration sensors are arranged on at least two or more crossing straight lines.

Figure 9A:
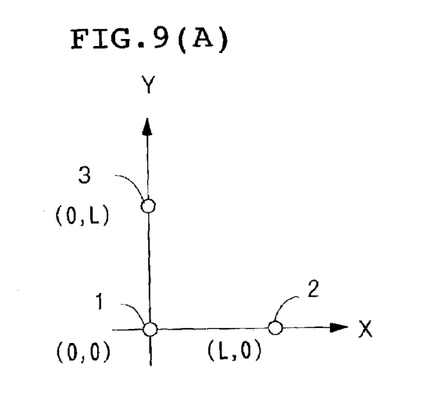
FIG. 9 is a diagram showing still another example of the arrangement of vibration sensors according to the present invention.

More specifically, when vibration sensors 1, 2 and 3 are arranged at coordinates (0,0), (L,0) and (0,L) as shown in FIG. 9(A), respectively, they can form two pairs of vibration sensors (1, 2) and (1, 3) arranged on different straight lines, thereby making it possible to obtain the direction θ of a vibration source.

Figure 9B:
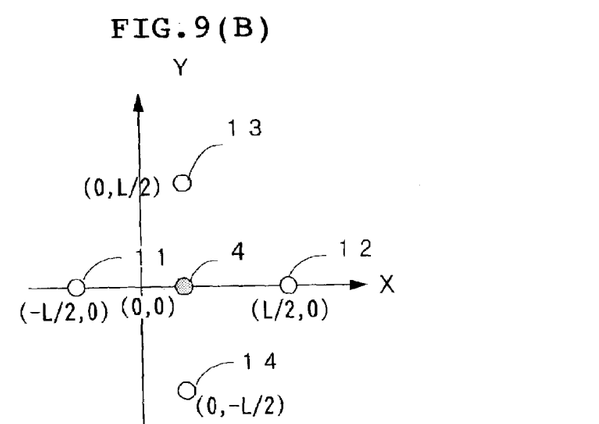

When a fifth vibration sensor 4 is placed at coordinates (0,0) in addition to the vibration sensors 11 to 14 of the embodiment shown in FIG. 3, as shown in FIG. 9(B), the vibration source direction θ can be calculated from a plurality of pairs of vibration sensors (11, 12), (13, 14), (11, 12), (4, 14), (4, 12) and (13, 14). Therefore, the values θ calculated from these pairs of vibration sensors are averaged to obtain the value of the vibration source direction θ, thereby making it possible to improve the measurement accuracy of the vibration source direction θ.

Figure 9C:
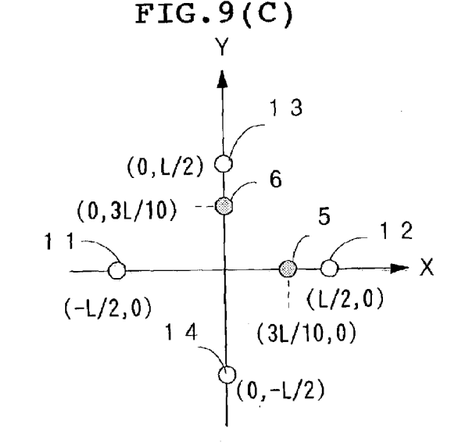

Alternatively, when vibration sensors 5 and 6 are placed at coordinates (3L/10,0) and coordinates (0, 3L/10) in addition to the above vibration sensors 11 to 14 as shown in FIG. 9(C), θ can be calculated from the pairs of vibration sensors (11, 12) and (13, 14) which are separate from each other by a distance L and pairs of vibration sensors (11, 5) and (6, 14) which are separate from each other by a distance 4L/5, thereby making it possible to improve the measurement accuracy of the vibration source direction θ.

Figure 9D:
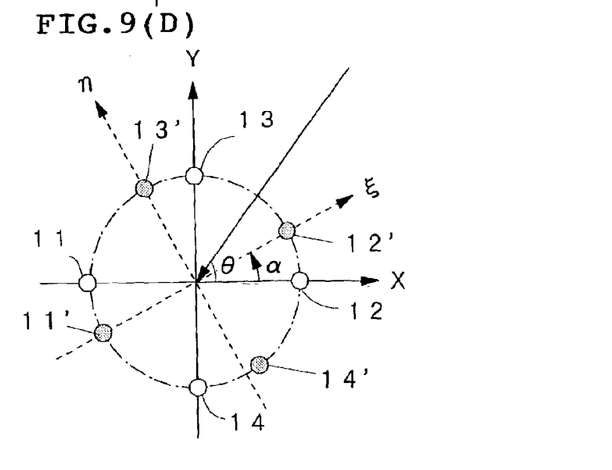

When vibration sensors 11' to 14' are installed at positions where the above vibration sensors 11 to 14 are turned at an angle α as shown in FIG. 9(D) in addition to the above sensors 11 to 14, the vibration source direction θ can be calculated from pairs of vibration sensors (11, 12) and (13, 14) arranged in the X-axis direction and the Y-axis direction which cross each other at a right angle and pairs of vibration sensors (11', 12') and (13', 14') which are arranged in the ξ-axis direction and the η-axis direction which intersect the above X axis and Y axis at the angle α. The measurement accuracy of the vibration source direction θ can be improved by averaging the above two θ values to obtain the value of the vibration source direction θ.

In the above embodiment, measurement is made by turning the vibration sensors 11 to 14 and the camera 15 at each measurement point. Even when the measurement is made only by moving the vibration detection means 10 to a plurality of points, or only by turning the vibration sensors 11 to 14 and the camera 15 at the same measurement point, the position of the measurement source can be specified.

It is needless to say that the distance L between vibration sensors is not limited to 0.6 m and suitably determined by the characteristics (such as the propagation speed of surface wave vibration), the properties of a vibration source and the like.

It is also possible to estimate the movement of the position of a vibration source by detecting vibration at predetermined time intervals at one measurement point or measurement angle to obtain the position of the vibration source at each measurement time.

As having been described above, since the vibration source probe system of the present invention comprises vibration detection means having at least three vibration sensors arranged on the same plane and vibration source estimation means for estimating a vibration source from phase differences or arrival time differences among the vibrations of surface waves detected by the vibration sensors and estimates the position of the vibration source from phase differences among output signals from the vibration sensors, the vibration source can be specified accurately and displayed.

A pair of vibration sensors which are separate from each other by a predetermined distance are arranged on two straight lines crossing each other at a right angle to obtain an arrival time difference between vibrations detected by the vibration sensors and specify a vibration source from the above arrival time difference. Therefore, the vibration source can be specified accurately with simple constitution.

The above vibration sensors are moved to a plurality of positions or turned to make measurements at a plurality of measurement points or a plurality of angles, thereby making it possible to improve the accuracy of specifying the position of the vibration source.

Further, the movement of the position of the vibration source can be estimated by detecting vibration at predetermined time intervals to obtain the position of the vibration source at each measurement time.

The absolute position on the ground of a vibration source can be specified by providing position specifying means such as GPS for measuring the absolute positions on the ground of the vibration sensors.

Since an image near the above estimated position of the vibration source is picked up to display the estimated position of the vibration source on the image. Therefore, the characteristics of the vibration source can be judged visually.

What is claimed is:

1. A vibration source probe system comprising:
   vibration detection means for detecting continuous vibrations or surface waves from a vibration source to provide output signals, said vibration detection means having at least three vibration sensors arranged on the same plane to form at least two pairs of vibration sensors arranged on two crossing straight lines; and
   vibration source estimation means for analyzing frequencies of the output signals from the at least two pairs of vibration sensors to determine phase differences for the at least two pairs of vibration sensors at a predetermined frequency and determined arrival time differences from the phase differences at the predetermined frequency and estimating a location of the vibration source based on a ratio of the phase differences or arrival time differences.

2. The vibration source probe system according to claim 1, wherein said two crossing straight lines cross each other at a right angle, vibration sensors of each of the at least two pairs being separated from each other at a predetermined distance, to obtain the arrival time differences between vibrations detected by the at least two pairs of vibration sensors in order to specify the location of the vibration source based on said ratio of the arrival time differences.

3. The vibration source probe system according to claim 1, wherein the vibration detection means detects the vibration at predetermined time intervals to estimate a movement of the vibration source.

4. The vibration source probe system according to claim 1 further comprising means for measuring an absolute position of the vibration detection means located on a ground.

5. The vibration source probe system according to claim 1, wherein the vibration detection means is moved to a plurality of positions.

6. The vibration source probe system according to claim 1, wherein the vibration detection means is made rotatable.

7. The vibration source probe system according to claim 1, further comprising image pick-up means for picking up an image near an estimated vibration source and display means for displaying a location of the estimated vibration source on the picked up image.

8. The vibration source probe system according to claim 7, wherein either one or both of a time change in a magnitude and a frequency spectrum of the vibration detected by the at least two pairs of vibration sensors are displayed on the display means.

9. The vibration source probe system according to claim 7, wherein a color of a symbol indicating the position of the vibration source displayed on the display means is changed by a level or a frequency of the vibration detected by the at least two pairs of vibration sensors.

10. The vibration source probe system according to claim 7, wherein a movement of a specified vibration source is displayed on the display means.

* * * * *